US010412976B2

(12) United States Patent
Medoff

(10) Patent No.: US 10,412,976 B2
(45) Date of Patent: *Sep. 17, 2019

(54) SACCHARIDES AND SACCHARIDE COMPOSITIONS AND MIXTURES

(71) Applicant: Xyleco, Inc., Wakefield, MA (US)

(72) Inventor: Marshall Medoff, Brookline, MA (US)

(73) Assignee: XYLECO, INC., Wakefield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/158,119

(22) Filed: May 18, 2016

(65) Prior Publication Data

US 2016/0262434 A1 Sep. 15, 2016

Related U.S. Application Data

(63) Continuation of application No. 14/554,887, filed on Nov. 26, 2014, now Pat. No. 9,364,015.

(60) Provisional application No. 62/055,349, filed on Sep. 25, 2014, provisional application No. 62/052,913, filed on Sep. 19, 2014.

(51) Int. Cl.
| | |
|---|---|
| *A23K 20/163* | (2016.01) |
| *A23L 2/60* | (2006.01) |
| *A61K 8/60* | (2006.01) |
| *A61K 31/7004* | (2006.01) |
| *A61Q 19/00* | (2006.01) |
| *A61K 47/26* | (2006.01) |
| *A61K 9/00* | (2006.01) |
| *A61K 9/08* | (2006.01) |
| *A61K 31/7016* | (2006.01) |
| *A61K 45/06* | (2006.01) |

(52) U.S. Cl.
CPC ............ *A23K 20/163* (2016.05); *A23L 2/60* (2013.01); *A61K 8/60* (2013.01); *A61K 9/0095* (2013.01); *A61K 9/08* (2013.01); *A61K 31/7004* (2013.01); *A61K 31/7016* (2013.01); *A61K 45/06* (2013.01); *A61K 47/26* (2013.01); *A61Q 19/00* (2013.01); *A23V 2002/00* (2013.01); *A61K 2800/10* (2013.01); *A61K 2800/5922* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 181,136 A | 8/1876 | Brandriff | |
| 3,844,890 A | 10/1974 | Horikoshi et al. | |
| 3,957,969 A | 5/1976 | Fujiyama et al. | |
| 4,220,721 A | 9/1980 | Emert et al. | |
| 4,242,455 A | 12/1980 | Muller et al. | |
| 4,435,307 A | 3/1984 | Barbesgaard et al. | |
| 4,470,851 A | 9/1984 | Paszner et al. | |
| 4,497,896 A | 2/1985 | Assarsson et al. | |
| 4,690,824 A | 9/1987 | Powell et al. | |
| 4,769,082 A | 9/1988 | Kumakura et al. | |
| 5,064,659 A | 11/1991 | Greenberg et al. | |
| 5,468,734 A | 11/1995 | Seri et al. | |
| 5,624,661 A | 4/1997 | Unger | |
| 5,869,029 A | 2/1999 | Graff-Andersen et al. | |
| 5,932,452 A | 8/1999 | Mustranta et al. | |
| 6,051,236 A | 4/2000 | Portman | |
| 6,451,123 B1 | 9/2002 | Saska et al. | |
| 6,737,258 B2 | 5/2004 | Hames et al. | |
| 7,807,419 B2 | 10/2010 | Hennessey et al. | |
| 9,364,015 B2 | 6/2016 | Medoff | |
| 10,045,552 B2 | 8/2018 | Medoff | |
| 2005/0164355 A1 | 7/2005 | Vlasenko et al. | |
| 2006/0140927 A1 | 6/2006 | Nonomura | |
| 2008/0020437 A1 | 1/2008 | Savarese | |
| 2008/0299631 A1 | 12/2008 | Peng et al. | |
| 2009/0042259 A1 | 2/2009 | Dale et al. | |
| 2009/0062232 A1 | 3/2009 | Fujikawa et al. | |
| 2009/0117635 A1 | 5/2009 | Bradley et al. | |
| 2010/0178670 A1 | 7/2010 | Smith et al. | |
| 2010/0200806 A1 | 8/2010 | Medoff et al. | |
| 2010/0266726 A1 | 10/2010 | Ogura et al. | |
| 2012/0100577 A1 | 4/2012 | Medoff et al. | |
| 2014/0011258 A1 | 1/2014 | Medoff et al. | |
| 2016/0082022 A1 | 3/2016 | Medoff | |

FOREIGN PATENT DOCUMENTS

| | | |
|---|---|---|
| CA | 2691883 A1 | 1/2009 |
| CN | 1076344 A | 9/1993 |
| CN | 101715940 A | 6/2010 |
| CN | 101715940 B | 7/2012 |
| CN | 103315261 | 9/2013 |
| CN | 103767952 | 5/2014 |
| CN | 103876115 | 6/2014 |

(Continued)

OTHER PUBLICATIONS

Zheng, CN 101715940 B, Jul. 25, 2012, machine translation.*
International Search Report and Written Opinion for International Patent Application No. PCT/US14/67603 dated Mar. 15, 2015 (10 pages).
Moraïs et al. "Deconstruction of Lignocellulose into Soluble Sugars by Native and Designer Cellulosomes," mBio, vol. 3, No. 6, 11 pages (2012).
Nanda et al., "Butanol and ethanol production from lignocellulosic feedstock: biomass pretreatment and bioconversion," Energy Science & Engineering, vol. 2, No. 3, pp. 138-148 (2014).
Hu et al., "Simultaneous utilization of glucose and xylose for lipid production by *Trichosporon cutaneum*," Biotechnology for Biofuels, 4:25, 8 pages (2011).

(Continued)

*Primary Examiner* — Layla D Berry
(74) *Attorney, Agent, or Firm* — Lando & Anastasi, LLP

(57) ABSTRACT

Described herein are products comprising a xylose (e.g., D-xylose or L-xylose and another sweetener such as glucose). Exemplary products include cosmetic products, oral care products, therapeutic products, nutraceutical products, diagnostic, beverages, animal food products, and human food products. Methods of making the xylose containing products from biomass is provided.

33 Claims, No Drawings

(56) References Cited

FOREIGN PATENT DOCUMENTS

| | | | |
|---|---|---|---|
| EP | 0458162 | A1 | 11/1991 |
| JP | 75030708 | B | 10/1970 |
| JP | S61-078390 | | 4/1986 |
| JP | H119897 | A | 1/1999 |
| JP | H1127614 | A | 1/1999 |
| JP | H1198971 | A | 4/1999 |
| JP | H11276149 | | 10/1999 |
| JP | 2000-005084 | A | 1/2000 |
| JP | 2000050840 | | 2/2000 |
| JP | 2006-029622 | A | 2/2006 |
| JP | 2006-087319 | A | 4/2006 |
| JP | 2006296224 | A | 11/2006 |
| JP | 2008-001178 | A | 1/2008 |
| JP | 2008011783 | A | 1/2008 |
| JP | 2008-054608 | A | 3/2008 |
| JP | 2008-521396 | A | 6/2008 |
| RU | 2144087 | C1 | 1/2000 |
| WO | 93/10213 | A1 | 5/1993 |
| WO | 97/33035 | A1 | 9/1997 |
| WO | WO-98/00098 | | 1/1998 |
| WO | WO-03/010339 | | 2/2003 |
| WO | WO-2004/015145 | | 2/2004 |
| WO | 2005/099854 | A1 | 10/2005 |
| WO | WO-2006/007691 | | 1/2006 |
| WO | 2006/024242 | A1 | 3/2006 |
| WO | 2006/056838 | A1 | 6/2006 |
| WO | 2006/110901 | A2 | 10/2006 |
| WO | WO-2007/009463 | | 1/2007 |
| WO | WO-2007084752 | | 7/2007 |
| WO | 2008/051349 | A2 | 5/2008 |
| WO | WO-2008/073186 | | 6/2008 |
| WO | WO 2008/112727 | | 9/2008 |
| WO | 2008/134037 | A1 | 11/2008 |
| WO | 2008/154468 | A1 | 12/2008 |
| WO | 2009/001205 | A2 | 12/2008 |
| WO | 2009/003167 | A1 | 12/2008 |
| WO | WO-2008/147396 | | 12/2008 |
| WO | WO-2009/012256 | | 1/2009 |
| WO | WO-2009/102256 | | 8/2009 |
| WO | WO-2010/093832 | | 8/2010 |
| WO | WO-2010135380 | | 11/2010 |
| WO | WO-2013096698 | A1 * | 6/2013 ............. C12P 19/14 |
| WO | WO-2013105033 | | 7/2013 |
| WO | WO-2014/138553 | | 9/2014 |
| WO | 2016/043789 | A1 | 3/2016 |

OTHER PUBLICATIONS

Carrasco et al., "Steam pretreatment and fermentation of the straw material "Paja Brava" using simultaneous saccharification and co-fermentation," Journal of Bioscience and Bioengineering, vol. 111, No. 2, pp. 167-174 (2011).
Da Silva et al., "Improvement of biotechnological xylitol production by glucose during cultive of Candida guilliermondii in sugarcane bagasse hydrolysate," Database Biosis (Online) Biosciences Information Service, Philadelphia. PA. US, XP002777381 Database accession No. PREV200700384808, abstract, 2 pages (Mar. 31, 2007).
Extended European Search Report for European Patent Application No. EP 15842356 dated Jan. 31, 2018 (11 pages).
Supplementary European Search Report for European Patent Application No. EP 14902223 dated Feb. 9, 2018 (11 pages).
Penttilä et al., "Xylan as limiting factor in enzymatic hydrolysis of nanocellulose," Bioresource Technology, vol. 129, pp. 135-141 (2013).
Portilla-Rivera et al., "Development of a factorial design to study the effect of the major hemicellulosic sugars on the production of surface-active compounds by L. pentosus," Database FSTA (Online) International Food Information Service (IFIS). Frankfurt-Main, Germany, Database accession No. FS-2010-02-Bi0227, XP002777382, abstract, 2 pages (Nov. 23, 2009).
Search Report and Written Opinion for Singaporean Patent Application No. 11201701959S dated Jan. 26, 2018; Search Completed Jan. 9, 2018 (10 pages).
Tianjin Lanshi Seasoning Co. Ltd., "Shark fin sauce used as seasoning, comprises winged turtle, seafood powder, L-cysteine hydrochloride, glucose, D-xylose, water, seafood essence, edible alcohol, potassium sorbate and carboxymethyl cellulose as thickening agent," Database WPI, Week 201457, Thomson Scientific, London, GB XP-002777383, 2 pages (Jun. 25, 2014).
AE Biofuels, "Next-Generation Cellulosic Ethanol Processes," Retrieved online Nov. 10, 2010, (4 pages) <http://web.archive.org/web/20080626200953/http://www.aebiofuels.com/cellulosic_ethanol.php>.
Aquarone, "Penicillin and Tetracycline as Contamination Control Agents in Alcoholic Fermentation of Sugar Cane Molasses," Applied Microbiology, vol. 8, pp. 263-268 (1960).
Beardmore et al., "Gamma-Ray Irradiation as a Pretreatment for the Enzymatic Hydrolysis of cellulose," Biotechnology Letters, 2(10), pp. 435-438 (1980).
Casey et al., "High Gravity Brewing: Nutrient Enhanced Production of High Concentrations of Ethanol by Brewing Yeast," Biotechnology Letters, vol. 5, No. 6, pp. 429-434 (1983).
Khan et al., "Effect of Electron-Beam Irradiation Pretreatment on the Enzymatic Hydrolysis of Softwood," Biotechnology and Bioengineering, 28, pp. 1449-1453 (1986).
Lin et al., "Ethanol fermentation from biomass resources: current state and prospects," Appl. Microbiol. Biotechnol., vol. 69, pp. 627-642 (2006).
MagnetoWiki, "Density of Sugar Solutions," accessed from http://wiki.houptlab.org/wiki/Density_of_Sugar_Solutions on Mar. 3, 2015 (1 page).
Renewable biological systems for alternative sustainable energy production (FAO Agricultural Services Bulletin—128) published 1997 (retrieved from the internet Jan. 23, 2017) http://www.fao.orq/docrep/w7241e/w7241eOO.htm#Contents> (102 pages).
Szczodrak et al., "Technology for Conversion of Lignocellulosic Biomass to Ethanol," Biomass and Bioenergy, vol. 10(5/6), pp. 367-375 (1996).
Yu et al., "Fermentation to ethanol of pentose-containing spent sulphite liquor," Biotechnology and Bioengineering, vol. 29, pp. 1144-1150 (1987).
Mechanical Translation of CN-1076344A, application published on Sep. 22, 1993 (3 pages).
International Search Report for International Application No. PCT/US15/47572 dated Nov. 24, 2015 (3 pages).
Written Opinion for International Application No. PCT/US15/47572 dated Nov. 24, 2015 (5 pages).
Baraldi, "Effect of Gamma Radiation on D-Glucose present in apple juice," Journal of Food Science, vol. 38, pp. 108-111 (1973).
Chang, "Star Anise: A Dominant Chinese Spice," Flavor & Fortune, 2003, Issue: 10(3) www.flavorandfortune.com/dataaccess/article.php?ID=421, (4 pages).

* cited by examiner

SACCHARIDES AND SACCHARIDE COMPOSITIONS AND MIXTURES

RELATED APPLICATIONS

This application is a continuation of U.S. application Ser. No. 14/554,887 filed Nov. 26, 2014, which claims priority to U.S. Provisional Application No. 62/052,913, filed Sep. 19, 2014; and U.S. Provisional Application 62/055,349, filed Sep. 25, 2014, all of which are incorporated herein by reference in their entirety.

FIELD OF THE INVENTION

The present invention relates generally to compositions including saccharides and mixtures of saccharides and related compounds. The present invention further generally relates to methods for producing the compositions described herein. The present invention also provides methods for using such compositions, e.g., as health care products, or as a sweetener in a product such as a beverage sweetener or syrup.

BACKGROUND OF THE INVENTION

Xylose is a natural sugar that is found (in polymeric form) in some woody materials such as straw, birch trees, pecan shells, cottonseed hulls, and corncobs. Xylose tastes sweet, and can inhibit the absorption of other sugars in the body. On the glycemic index, which measures the rate of the absorption of sugar by the body, sugar is a 100 while xylose is only a 7. Moreover, xylose does not contribute to tooth decay. Xylose is safe for use in foods and has additional desirable properties including beneficial antibacterial and antifungal activity. However, xylose can be expensive to produce, making it more difficult to incorporate into products such as food and beverage products. Artificial sweeteners and genetically modified foods can destroy the body's flora and can encourage the wrong type of bacterial overgrowth, resulting in incorrect physiological responses in the human body, such as in your GI tract, which can lead to glucose intolerance (Nature 514, 191-186, October 2014).

SUMMARY OF THE INVENTION

Applicant has discovered that health benefits are increased and are associated with the proper use of compositions of sugars and/or sweeteners and related compounds. Health benefits are improved by consideration of the physiology of the use of sugars and sweeteners and/or related compounds, e.g., sugar alcohols. Applicant has further discovered that, for example, both corn and cane sugars have been manufactured as only 6-carbon products or disaccharides of 6-carbon sugars even though the corn and sugar cane plants themselves carry both 6-carbon sugars and 5-carbon sugars (in polymeric form). It is a concern of the applicant that the benefit of using both 5- and 6-carbon sugars in the proper ratio increases good health and nutritional well-being.

While it is generally understood that the consumption of unprocessed or lightly processed foods, such as whole, raw, unpeeled fruits and vegetables, is associated with substantial health benefits, such as a reduction in cardiovascular disease, lowering of blood pressure, improved brain activity, reduction in incidence of cancer, improved intestinal health and improved vision, it is generally poorly understood as why this is the case. Applicant believes that such benefits, at least in part, are associated with the fact that such whole foods have a more balanced and natural carbohydrate content in terms of simple sugars, e.g., glucose, mannose, galactose and xylose and polymeric sugars, e.g., cellulose and hemicellulose. Processed foods generally enrich foods in unnatural ratios of sugars. Perturbing the natural ratios of sugars or enriching one or more sugars can have significant health consequences, including many that are non-beneficial.

Applicant believes that although only small amounts of hemicellulose is broken down to simple sugars, e.g., xylose, mannose, galactose and glucose, along the digestive tract, even small amounts of these sugars not normally found in processed foods can induce positive health benefits. Applicant suggests that the breakdown of hemicellulose is a in the digestive tract is an example of a natural force action as such breakdown naturally stimulates various biological processes in those organisms in the digestive tract that would not be so stimulated if not for the presence of the described hemicellulose sugars. Such stimulation can allow for the uptake of more nutrients, such as micronutrients, and produce health benefits in the body.

Applicant has further discovered cost efficient ways to make compositions that include small sugars, such as xylose. Described herein are products and compositions that include xylose. Exemplary products and compositions include syrups and beverage products comprising xylose. In some embodiments, the compositions include xylose and one of more of any saccharide, such as a mono-, di-, tri- or oligosaccharide, or an associated sugar alcohol. The saccharides can be in any stereoisomeric form. The saccharides include 3, 4, 5, 6, or more e.g., 7, 8 or more, e.g., 9-16 carbon atoms. Exemplary saccharides include glyceraldehyde, dihydroxyacetone, erythose, ribose, ribulose, arabinose, glucose, fructose, manose, galactose, corn syrup, high fructose corn syrup, sedoheptulose, sucrose, maltose, lactose, and cellobiose. In some embodiments the composition includes xylose and glucose. In other embodiments, the compositions include xylose and glucose, along with other saccharides, such as galactose, sucrose, arabinose, mannose, fructose and oligomeric saccharides, such as di-, tri-, tetra-, penta- and hexasaccharides. In particular embodiments, the composition includes greater than 75 percent by weight glucose plus xylose, e.g., greater than 80, 85, 90, or greater than 95 percent by weight glucose plus xylose.

Advantages can include one or more of the following benefits. Low glycemic index compositions are provided. The deleterious effects related to the overuse of some sugars, such as glucose, sucrose, fructose, corn syrup, corn sugar and high fructose corn syrup (HFCS), can be reduced, even with the addition of relatively small amounts of xylose. The deleterious effects related to the use or overuse of sugar substitutes, such as stevia, aspartame, sucralose, neotame, acesulfame potassium (Ace-K), saccharin, advantame and cyclamates, can be reduced. The compositions can be useful for those with diabetes and can be useful for reducing obesity. The compositions can be blended with sugar substitutes and sugar alcohols. Unique mouth-feel products can be produced with consumer appeal. Synergistically sweet compositions can be provided with blends of xylose and any compound described herein. Compositions can be provided that have a longer shelf life and that have a lower tendency to be contaminated with microorganisms. Non-crystallizing compositions can be provided. Compositions can be provided that are useful in cooking and are easier to brown during cooking. The compositions can have oral health benefits, such as the reduction of dental caries and gingivitis.

The compositions can be useful in fighting cancer. The compositions can be useful in balancing gut bacteria, which can lead to improved health, better digestion, improved memory and mental health. The compositions can reduce risk of stroke, diabetes, obesity, metabolic disease, cardiovascular disease and high blood pressure. The compositions can also improve vision.

In one aspect, the invention features a product comprising xylose and another material described herein, e.g., another carbohydrate, sugar, sweetener or related compounds;
a. wherein the product is selected from the group consisting of a cosmetic product, oral care product, therapeutic product, nutraceutical product, diagnostic, beverage, animal food product, and human food product.

In an embodiment, the other material or materials, e.g., carbohydrate, sugar or sweetener is selected from the group consisting of glyceraldehyde, dihydroxyacetone, erythose, ribose, ribulose, arabinose, glucose, fructose, manose, galactose, corn syrup, high fructose corn syrup, sedoheptulose, sucrose, maltose, lactose, cellobiose, stevia, aspartame, sucralose, neotame, acesulfame potassium (Ace-K), saccharin, advantame and cyclamates.

In an embodiment, the cosmetic product is lip stick, lip gloss, face and body preparations, or soaps. In an embodiment, the oral care product is dental floss, toothpaste, shampoo, or mouth rinse.

In an embodiment, the product is a therapeutic product such as a neutraceutical or pharmaceutical product. Exemplary therapeutic products include flu and cold preparations, dietary supplements, surgical preparations, procedure preparations, fibers, such as cellulosic and lignocellulosic fibers and fiber supplements, pain relievers, and nasal spray.

In an embodiment, the product is a diagnostic product such as an imaging preparation, e.g., CT scan imaging preparation.

In an embodiment, the product is a beverage such as tea, flavored water, alcohol (e.g., beer, wine or a spirit), a drink mix such as an alcohol mixer, an energy drink, coffee, a coffee flavored drink, a coffee product, coconut water, soda pop, or a sports drink. In an embodiment, the beverage has a pH of from about 3 to about 9 (e.g., from about 3.5 to about 8.5 or from about 4 to about 7.5). In an embodiment, the product is an animal food product, such as dog, cat, canine, or equine food.

In an embodiment, product is a human food product, for example a packaged food product, a candy (e.g., a jelly candy), a dessert or snack, a condiment, or a frozen treat. Exemplary packaged food products include baby food desserts and snacks such as, seasonings, sauces, cheese, vegetables, nuts and nut mixes, cookies, pastries, fruit flavored snacks, pancakes, waffles, hot cocoa mix, donuts, noodles such as egg noodles, chips, potato chips, tortilla chips, corn chips, rice cakes, oatmeals, cereals, rice mixtures, cake mixes, chili, meats, e.g., deli meats, pasta, meals ready to eat, sports bars, and energy bars. In an embodiment, the food product is a frozen treat. Exemplary frozen treats include ice cream, ice milk, sorbet, sherbet, and frozen pops. In an embodiment the product is a candy. Exemplary candies include gelatin candies, hard and soft candies, chocolate, candy bars, lollypops, and caramel.

In an embodiment, the food product is a condiment. Exemplary condiments include: seasonings, sauces, mayonnaise, mustard, salad dressings, chip dip, and chip sauces.

In an embodiment, the product includes an additional carbohydrate or sugar (e.g., another sugar). In an embodiment, less than 10 percent by weight of the product (e.g., less than 5 percent, less than 2 percent or less than 1 percent) includes the other sugar, e.g., sweetener (e.g., glucose or fructose). In an embodiment, less than 10 percent of the calorie content of the product (e.g., less than 5 percent, less than 2 percent or less than 1 percent) is from the other sugar, e.g., sweetener (e.g., glucose or fructose). In an embodiment, the glycemic index of the product is less than 50, 40, 30, 15, such as less than 10.

In another aspect, the invention features a product comprising xylose and glucose, wherein the product is selected from the group consisting of a cosmetic product, oral care product, therapeutic product, neutraceutical product, diagnostic, beverage, animal food product, and human food product.

In an embodiment, the cosmetic product is lip stick, lip gloss, face and body preparations, or soaps. In an embodiment, the oral care product is dental floss, toothpaste, shampoo, or mouth rinse.

In an embodiment, the product is a therapeutic product such as a neutraceutical or pharmaceutical product. Exemplary therapeutic products include flu and cold preparations, dietary supplements, surgical preparations, procedure preparations, fibers, such as cellulosic and lignocellulosic fibers and fiber supplements, pain relievers, and nasal spray.

In an embodiment, the product is a diagnostic product such as an imaging preparation, e.g., CT scan imaging preparation.

In an embodiment, the product is a beverage such as tea, flavored water, alcohol (e.g., beer, wine or a spirit), a drink mix such as an alcohol mixer, an energy drink, coffee, a coffee flavored drink, a coffee product, coconut water, soda pop, or a sports drink. In an embodiment, the beverage has a pH of from about 3 to about 9 (e.g., from about 3.5 to about 8.5 or from about 4 to about 7.5).

In an embodiment, the product is an animal food product, such as dog, cat, canine, or equine food.

In an embodiment, product is a human food product, for example a packaged food product, a candy (e.g., a jelly candy), a dessert or snack, a condiment, or a frozen treat. Exemplary packaged food products include baby food desserts and snacks such as, seasonings, sauces, cheese, vegetables, nuts and nut mixes, cookies, pastries, fruit flavored snacks, pancakes, waffles, hot cocoa mix, donuts, noodles such as egg noodles, chips, potato chips, tortilla chips, corn chips, rice cakes, oatmeals, cereals, rice mixtures, cake mixes, chili, meats, e.g., deli meats, pasta, meals ready to eat, sports bars, and energy bars. In an embodiment, the food product is a frozen treat. Exemplary frozen treats include ice cream, ice milk, sorbet, sherbet, and frozen pops. In an embodiment the product is a candy. Exemplary candies include gelatin candies, hard and soft candies, chocolate, candy bars, lollypops, and caramel.

In an embodiment, the food product is a condiment. Exemplary condiments include: seasonings, sauces, mayonnaise, mustard, salad dressings, chip dip, and chip sauces.

In an embodiment, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50. In an embodiment, the glycemic index of the product is less than 50, 40, 30, 15, such as less than 10.

In an embodiment, less than 10 percent by weight of the product includes glucose. In an embodiment, less than 10 percent of the calorie content of the product is from glucose. In an embodiment, the glycemic index of the product is less than 50, 40, 30, 15, such as less than 10.

In another aspect, the invention features a method of making a product, the method comprising, saccharifying a cellulosic or lignocellulosic biomass to liberate a sugar;

purifying the liberated sugar; and adding the purified sugars to a product, wherein the product comprises a cosmetic product, oral care product, therapeutic product, neutraceutical product, diagnostic, beverage, animal food product, or human food product.

In an embodiment, the cosmetic product is lip stick, lip gloss, face and body preparations, or soaps. In an embodiment, the oral care product is dental floss, toothpaste, shampoo, or mouth rinse.

In an embodiment, the product is a therapeutic product such as a neutraceutical or pharmaceutical product. Exemplary therapeutic products include flu and cold preparations, dietary supplements, surgical preparations, procedure preparations, fibers, such as cellulosic and lignocellulosic fibers and fiber supplements, pain relievers, and nasal spray.

In an embodiment, the product is a diagnostic product such as an imaging preparation, e.g., CT scan imaging preparation.

In an embodiment, the product is a beverage such as tea, flavored water, alcohol (e.g., beer, wine or a spirit), a drink mix such as an alcohol mixer, an energy drink, coffee, a coffee flavored drink, a coffee product, coconut water, soda pop, or a sports drink. In an embodiment, the beverage has a pH of from about 3 to about 9 (e.g., from about 3.5 to about 8.5 or from about 4 to about 7.5).

In an embodiment, the product is an animal food product, such as dog, cat, canine, or equine food.

In an embodiment, product is a human food product, for example a packaged food product, a candy (e.g., a jelly candy), a dessert or snack, a condiment, or a frozen treat. Exemplary packaged food products include baby food desserts and snacks such as, seasonings, sauces, cheese, vegetables, nuts and nut mixes, cookies, pastries, fruit flavored snacks, pancakes, waffles, hot cocoa mix, donuts, noodles such as egg noodles, chips, potato chips, tortilla chips, corn chips, rice cakes, oatmeals, cereals, rice mixtures, cake mixes, chili, meats, e.g., deli meats, pasta, meals ready to eat, sports bars, and energy bars. In an embodiment, the food product is a frozen treat. Exemplary frozen treats include ice cream, ice milk, sorbet, sherbet, and frozen pops. In an embodiment the product is a candy. Exemplary candies include gelatin candies, hard and soft candies, chocolate, candy bars, lollypops, and caramel.

In an embodiment, the food product is a condiment. Exemplary condiments include: seasonings, sauces, mayonnaise, mustard, salad dressings, chip dip, and chip sauces.

In an embodiment, the liberated sugar comprises xylose. In an embodiment, the method includes liberating and purifying a plurality of sugars, wherein the sugars comprise xylose and glucose. In an embodiment, the plurality of sugars is purified as a mixture. In an embodiment, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50.

In an embodiment, the xylose and glucose are co-produced. Co-produced, as used herein means made in the same reaction or obtained from the same precursor molecule such as cellulose, and subjected to at least one common purification procedure (e.g., filtration). In embodiments a common purification procedure includes producing a product having at least 5% by weight of xylose and glucose (e.g., at least 10%, at least 15%, at least 20%, at least 30%, at least 40%, at least 50%, at least 60%, at least 70% or at least 75%).

In another aspect, the invention features a method of making a product, the method comprising, adding a blend of sugars comprising xylose obtained from saccharifying cellulosic or lignocellulosic biomass to a product, the product being selected from the group consisting of a cosmetic product, oral care product, therapeutic product, neutraceutical product, diagnostic, beverage, animal food product, and human food product.

In an embodiment, the cosmetic product is lip stick, lip gloss, face and body preparations, or soaps. In an embodiment, the oral care product is dental floss, toothpaste, shampoo, or mouth rinse.

In an embodiment, the product is a therapeutic product such as a neutraceutical or pharmaceutical product. Exemplary therapeutic products include flu and cold preparations, dietary supplements, surgical preparations, procedure preparations, fibers, such as cellulosic and lignocellulosic fibers and fiber supplements, pain relievers, and nasal spray.

In an embodiment, the product is a diagnostic product such as an imaging preparation, e.g., CT scan imaging preparation.

In an embodiment, the product is a beverage such as tea, flavored water, alcohol (e.g., beer, wine or a spirit), a drink mix such as an alcohol mixer, an energy drink, coffee, a coffee flavored drink, a coffee product, coconut water, soda pop, or a sports drink. In an embodiment, the beverage has a pH of from about 3 to about 9 (e.g., from about 3.5 to about 8.5 or from about 4 to about 7.5).

In an embodiment, the product is an animal food product, such as dog, cat, canine, or equine food.

In an embodiment, product is a human food product, for example a packaged food product, a candy (e.g., a jelly candy), a dessert or snack, a condiment, or a frozen treat. Exemplary packaged food products include baby food desserts and snacks such as, seasonings, sauces, cheese, vegetables, nuts and nut mixes, cookies, pastries, fruit flavored snacks, pancakes, waffles, hot cocoa mix, donuts, noodles such as egg noodles, chips, potato chips, tortilla chips, corn chips, rice cakes, oatmeals, cereals, rice mixtures, cake mixes, chili, meats, e.g., deli meats, pasta, meals ready to eat, sports bars, and energy bars. In an embodiment, the food product is a frozen treat. Exemplary frozen treats include ice cream, ice milk, sorbet, sherbet, and frozen pops. In an embodiment the product is a candy. Exemplary candies include gelatin candies, hard and soft candies, chocolate, candy bars, lollypops, and caramel.

In an embodiment, the food product is a condiment. Exemplary condiments include: seasonings, sauces, mayonnaise, mustard, salad dressings, chip dip, and chip sauces.

In an embodiment, the blend of sugars comprises glucose. In an embodiment, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50.

In an embodiment, the product described herein has a glycemic index relative to the product that does not include xylose which is lower by at least 5% (e.g., at least 10%, at least 15%, at least 20%, at least 30%, at least 40%, or at least 50%).

In an embodiment, the xylose and glucose are co-produced. In embodiments a common purification procedure includes producing a product having at least 5% by weight of xylose and glucose (e.g., at least 10%, at least 15%, at least 20%, at least 30%, at least 40%, at least 50%, at least 60%, at least 70% or at least 75%).

In another aspect, the invention features a method of combining a co-produced mixture of xylose and glucose with a component in a product described herein.

In another aspect, the invention features receiving a co-produced mixture of xylose and glucose from an entity that produces or distributes co-produced a mixture of xylose and glucose and combining with a component to produce a product described herein.

In another aspect, the invention features a food grade or cosmetic grate composition of co-produced xylose and glucose.

In one aspect, the disclosure features an aqueous composition comprising food grade xylose, wherein the composition can be substantially free of solid materials having a diameter of greater than 1000 nm and wherein the composition can have a color of less than about 100 as measured by the Platinum-Cobalt method.

In some embodiments, the composition can be substantially free of ethanol. In some embodiments, the composition further comprises glucose. In some embodiments, the composition can have a viscosity of from 5,000 to 75,000 at a concentration of 60 percent by weight at a temperature of 20 degrees Celsius. In some embodiments, the composition can be a syrup. In some embodiments, the composition can have a glycemic index of less than or equal to than 30. In some embodiments, the xylose can have a concentration of from 30 to 55 percent by weight. In some embodiments, the glucose can have a concentration of from 35 to 50 percent by weight. In some embodiments, the xylose can have a concentration of from 40 to 50 and the glucose has a concentration of from 30 to 50 percent by weight. In some embodiments, the composition can be substantially free of lignin. In some embodiments, the composition can be substantially free of cellulose. In another aspect, the disclosure features liquid compositions comprising xylose, wherein the composition can have a turbidity below 10 NTU.

In another aspect, the disclosure features liquid compositions comprising food grade xylose, wherein the glycemic index can be less than 30.

In some embodiments, the liquid composition further comprises glucose. In another aspect, the disclosure features a beverage comprising xylose. In some embodiments, the beverage can be a carbonated beverage. In some embodiments, the beverage is an alcoholic beverage. In some embodiments, the beverage can further comprise glucose. In some embodiments, the beverage can further comprise a colorant. In some embodiments, the beverage can further comprise an electrolyte. In some embodiments, the beverage can further comprise a vitamin. In another aspect, the disclosure features chewing gum comprising xylose. In another aspect, the disclosure features a dentifrice comprising xylose. In another aspect, the disclosure features a mouth rinse comprising xylose.

Any composition described herein can be used in any form desired. For example, any composition, with or without additives described herein, can be in the form of a pill, tablet or capsule. Compositions can also be, for example, in the form of solutions, e.g., medical solutions, such as intravenous solutions or diagnostic solutions, for example, for the study of malabsorption of carbohydrates, industrial solutions, biological solutions, such as biological media, and chemical solutions, e.g., as an intermediate, such as a solution that can be converted to a mixture of xylitol and sorbitol via hydrogenation.

The products described herein can include any one or more of the following features. The product can be selected from a cosmetic product, oral care product, therapeutic product, nutraceutical product, diagnostic, beverage, animal food product, and human food product. In an embodiment, the cosmetic product is lip stick, lip gloss, face and body preparations, or soaps. In an embodiment, the oral care product is dental floss, toothpaste, shampoo, or mouth rinse.

In an embodiment, the product is a therapeutic product such as a neutraceutical or pharmaceutical product. Exemplary therapeutic products include flu and cold preparations, dietary supplements, surgical preparations, procedure preparations, fibers, such as cellulosic and lignocellulosic fibers and fiber supplements, pain relievers, and nasal spray.

In an embodiment, the product is a diagnostic product such as an imaging preparation, e.g., CT scan imaging preparation.

In an embodiment, the product is a beverage such as tea, flavored water, alcohol (e.g., beer, wine or a spirit), a drink mix such as an alcohol mixer, an energy drink, coffee, a coffee flavored drink, a coffee product, coconut water, soda pop, or a sports drink. In an embodiment, the beverage has a pH of from about 3 to about 9 (e.g., from about 3.5 to about 8.5 or from about 4 to about 7.5). In an embodiment, the product is an animal food product, such as dog, cat, canine, or equine food.

In an embodiment, product is a human food product, for example a packaged food product, a candy (e.g., a jelly candy), a dessert or snack, a condiment, or a frozen treat. Exemplary packaged food products include baby food desserts and snacks such as, seasonings, sauces, cheese, vegetables, nuts and nut mixes, cookies, pastries, fruit flavored snacks, pancakes, waffles, hot cocoa mix, donuts, noodles such as egg noodles, chips, potato chips, tortilla chips, corn chips, rice cakes, oatmeals, cereals, rice mixtures, cake mixes, chili, meats, e.g., deli meats, pasta, meals ready to eat, sports bars, and energy bars. In an embodiment, the food product is a frozen treat. Exemplary frozen treats include ice cream, ice milk, sorbet, sherbet, and frozen pops. In an embodiment the product is a candy. Exemplary candies include gelatin candies, hard and soft candies, chocolate, candy bars, lollypops, and caramel.

In an embodiment, the food product is a condiment. Exemplary condiments include: seasonings, sauces, mayonnaise, mustard, salad dressings, chip dip, and chip sauces.

In an embodiment, the product includes an additional carbohydrate or sugar (e.g., another sugar). In an embodiment, less than 10 percent by weight of the product (e.g., less than 5 percent, less than 2 percent or less than 1 percent) includes the other sugar, e.g., sweetener (e.g., glucose or fructose). In an embodiment, less than 10 percent of the calorie content of the product (e.g., less than 5 percent, less than 2 percent or less than 1 percent) is from the other sugar, e.g., sweetener (e.g., glucose or fructose). In an embodiment, the glycemic index of the product is less than 50, 40, 30, 15, such as less than 10.

The product can include an additional material described herein, e.g., another carbohydrate, sugar or sweetener. Exemplary carbohydrates, sugars and sweeteners include glyceraldehyde, dihydroxyacetone, erythose, ribose, ribulose, arabinose, glucose, fructose, manose, galactose, corn syrup, high fructose corn syrup, sedoheptulose, sucrose, maltose, lactose, cellobiose, stevia, aspartame, sucralose, neotame, acesulfame potassium (Ace-K), saccharin, advantame and cyclamates.

In an embodiment, the product includes an additional carbohydrate or sugar (e.g., another sugar). In an embodiment, less than 10 percent by weight of the product (e.g., less than 5 percent, less than 2 percent or less than 1 percent) includes the other sugar, e.g., sweetener (e.g., glucose or fructose). In an embodiment, less than 10 percent of the calorie content of the product (e.g., less than 5 percent, less than 2 percent or less than 1 percent) is from the other sugar, e.g., sweetener (e.g., glucose or fructose). In an embodiment, the glycemic index of the product is less than 50, 40, 30, 15, such as less than 10.

In an embodiment, the product includes both xylose and glucose.

In an embodiment, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50. In an embodiment, the glycemic index of the product is less than 50, 40, 30, 15, such as less than 10.

In an embodiment, less than 10 percent by weight of the product includes glucose. In an embodiment, less than 10 percent of the calorie content of the product is from glucose. In an embodiment, the glycemic index of the product is less than 50, 40, 30, 15, such as less than 10. In an embodiment, the product described herein has a glycemic index relative to the product that does not include xylose which is lower by at least 5% (e.g., at least 10%, at least 15%, at least 20%, at least 30%, at least 40%, or at least 50%).

In an embodiment, the product is made from a method wherein a liberated sugar comprises xylose. In an embodiment, the method includes liberating and purifying a plurality of sugars, wherein the sugars comprise xylose and glucose. In an embodiment, the plurality of sugars is purified as a mixture. In an embodiment, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50.

In an embodiment, the product includes a blend of sugars comprising glucose. In an embodiment, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50.

DETAILED DESCRIPTION

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "biomass", as used herein, refers to any non-fossilized, organic matter. The various types of biomass include plant biomass (e.g., lignocellulosic and cellulosic biomass), microbial biomass, animal biomass (any animal by-product, animal waste, etc.) and municipal waste biomass (residential and light commercial refuse with recyclables such as metal and glass removed). Plant biomass refers to any plant-derived organic matter (woody or non-woody). Plant biomass can include, but is not limited to, agricultural or food crops (e.g., sugarcane, sugar beets or corn kernels) or an extract therefrom (e.g., sugar from sugarcane and corn starch from corn), agricultural crop wastes and residues such as corn stover, wheat straw, rice straw, sugar cane bagasse, and the like. Plant biomass further includes, but is not limited to, trees, woody energy crops, wood wastes and residues such as softwood forest thinnings, barky wastes, sawdust, paper and pulp industry waste streams, wood fiber, and the like. Additionally, grass crops, such as switchgrass and the like have potential to be produced on a large-scale as another plant biomass source. For urban areas, the best potential plant biomass feedstock includes yard waste (e.g., grass clippings, leaves, tree clippings, and brush) and vegetable processing waste.

The term "biomass degrading enzymes", as used herein, refers to enzymes that break down components of the biomass matter described herein into intermediates or final products. For example, biomass-degrading enzymes include at least ligninases, endoglucancases, cellobiases, xylanases, and cellobiohydrolases. Biomass-degrading enzymes are produced by a wide variety of microorganisms, and can be isolated from the microorganisms, such as *T. reesei*.

The term "cellobiase", as used herein, refers to an enzyme that catalyzes the hydrolysis of a dimer, trimer, tetramer, pentamer, hexamer, heptamer, octamer, or an oligomer of glucose, or an oligomer of glucose and xylose, to glucose and/or xylose. For example, the cellobiase is beta-glucosidase, which catalyzes beta-1,4 bonds in cellobiose to release two glucose molecules.

The term "cellobiase activity", as used herein, refers to activity of a category of cellulases that catalyze the hydrolysis of cellobiose to glucose, e.g., catalyzes the hydrolysis of beta-D-glucose residues to release beta-D-glucose. Cellobiase activity can be determined according to the assays described herein, e.g., in Example 6. One unit of cellobiase activity can be defined as [glucose] g/L/[Cel3a] g/L/30 minutes.

The term "cellobiohydrolase" as used herein, refers to an enzyme that hydrolyzes glycosidic bonds in cellulose. For example, the cellobiohydrolase is 1,4-beta-D-glucan cellobiohydrolase, which catalyzes the hydrolysis of 1,4-beta-D-glucosidic linkages in cellulose, cellooligosaccharides, or any beta-1,4-linked glucose containing polymer, releasing oligosaccharides from the polymer chain The term "endoglucanase" as used herein, refers to an enzyme that catalyzes the hydrolysis of internal □-1,4 glucosidic bonds of cellulose. For example, the endoglucanase is endo-1,4-(1,3; 1,4)-beta-D-glucan 4-glucanohydrolase, which catalyses endohydrolysis of 1,4-beta-D-glycosidic linkages in cellulose, cellulose derivatives (such as carboxymethyl cellulose and hydroxyethyl cellulose), lichenan, beta-1,4 bonds in mixed beta-1,3 glucans such as cereal beta-D-glucans or xyloglucans, and other plant material containing cellulosic components.

The term "ligninase" as used herein, refers to an enzyme that catalyzes the breakdown of lignin, commonly found in the cell walls of plants, such as by an oxidation reaction.

All references (e.g., patents, patent applications, publications) cited herein are incorporated by reference herein in their entirety for all that they contain.

Compositions and Products

Described herein are compositions and products, e.g., a solid, liquid or vaporous product, that includes xylose, and in some embodiments, xylose and glucose, optionally along with other saccharides, e.g., smaller amounts of other saccharides. Health benefits are associated with the compositions and products described herein. In some embodiments, the product is a consumer product such as a food or beverage. In some embodiments, the product is a component used in a consumer product such as a food or beverage, for example, a syrup used in a drink such as a cola, sports beverage, or flavored water (e.g., vitamin water). Using processes described herein, biomass material can be converted to one or more products, including xylose. In some embodiments the product includes a mixture of xylose and glucose in a cost efficient manner. Such products can be incorporated into products such as a beverage or a syrup. Other examples that can include the saccharide compositions described herein include, bake goods, chewing gum or oral compositions, including toothpastes and mouthrinses.

In an embodiment, the product is a cosmetic product, oral care product, therapeutic product, nutraceutical product, diagnostic, beverage, animal food product, or human food product. Other specific examples of compositions and products include ice cream, ice milk, sorbet, sherbet, gelatin candies, baby food, animal food, e.g., dog, cat, canine, or equine food, seasonings, sauces, cosmetics, dietary supplements, lip stick, lip gloss, face and body preparations, pharmaceuticals, such as flu and cold preparations, nutraceuticals, surgical preparations, procedure preparations, imaging preparations, e.g., CT scan imaging preparations, pain relievers, nasal spray, cheese, vegetables, mayonnaise, mustard, salad dressings, nuts and nut mixes, cookies, pastries, fruit flavored snacks, pancakes, waffles, hot cocoa mix, caramel, shampoo, dental floss, donuts, egg noodles, lollypops, frozen pops, soda pop, chips, potato chips, tortilla chips, corn chips, sports drinks, rice cakes, oatmeals, teas, cereals, rice mixtures, flavored water, alcohol, alcohol mixers, soaps, energy drinks, coffee, coffee flavored drinks, coffee products, cake mixes, chili, chip dip, chip sauces, fibers, such as cellulosic and lignocellulosic fibers and fiber supplements, meats, e.g., deli meats, drink mixes, pasta, meals ready to eat, coconut water, candies, e.g., hard and soft candies, chocolate, candy bars, sports bars and energy bars.

In an aspect, the product is a food composition, e.g., including food grade xylose, xylose plus glucose or xylose and glucose plus small amounts, e.g., less than 10 percent, less than 5 percent, less than 2 percent or less than 1 percent of other saccharides. In some embodiments the product further includes glucose, for example, food grade glucose. "Food grade," as used herein, refers to the minimum standard for a substance (e.g., xylose or glucose) to qualify as fit for human consumption or permitted to come in contact with food. These guidelines are defined by the U.S. Department of Agriculture (USDA) and the Food Safety and Inspection Service (FSIS).

Compositions and products described herein can have one or more of the following properties: the composition can be free or substantially free of certain components (e.g., solids, impurities, or processing by-products), have a defined color limit, or have certain defined physical properties such as concentration, turbidity, conductivity, viscosity, etc. In embodiments, where the composition or product includes both xylose and glucose, each of the xylose and glucose can be present in the composition or product in a ratio as defined herein.

A composition or product described herein can be made using a process described herein.

In some embodiments, the a product or a composition comprising xylose as described herein (e.g., a purified composition comprising xylose or xylose and glucose) is substantially free of a solid component, for example, a composition such as a liquid can include less than about 1 percent suspended solids, such as less about 0.75 percent, less than about 0.5 percent, less than about 0.4 percent, less than about 0.3 percent, less than about 0.25 percent, less than about 0.20 percent, less than about 0.15 percent, less than about 0.10 percent, less than about 0.05 percent, less than about 0.025 percent, or even less than about 0.010 percent. In some embodiments, a suspended solid in a composition described herein can have a particle size range of from about 0.05 micron to about 50 micron, such as from about 0.1 micron to about 25 micron, from about 0.2 micron to about 10 micron, from about 0.22 micron to about 5 micron, or from about 0.25 micron to about 1 micron. In an embodiment, the composition or product substantially free of a solid component is formulated as a beverage.

In an embodiment, the composition or product (e.g., a composition comprising xylose or a combination of xylose) is substantially free of a fermentation product such as ethanol. In an embodiment, the composition is substantially free of polysaccharide or oligosaccharide (e.g., cellulose). In yet other embodiments, the compositions or products include from about 0.1 to about 5 percent by weight, such as between about 0.2 and 2 percent oligosaccharides. In an embodiment, the composition or product is mixed with additional components to form a food or beverage product.

In an embodiment, a composition or product described herein can have a color of less than about 100 as measured by the Platinum-Cobalt method, such as less than about 50, less than about 40, less than about 30, less than about 20, less than about 10, less than about 5 and even less than about 1.

In an embodiment, a composition or product described herein has a concentration of xylose of at least about 50 g/L (e.g., at least about 100 g/L, at least about 150 g/L, at least about 200 g/L, at least about 250 g/L, at least about 300 g/L, at least about 350 g/L, at least about 400 g/L, at least about 450 g/L). In an embodiment, a composition or product described herein has a concentration of xylose of from about 50 g/L to about 500 g/L, such as from about 100 g/L to about 400 g/L, from about 150 g/L to about 350 g/L or from about 175 g/L to about 275 g/L.

In some embodiments, a composition or product is produced from a biomass liquid entering a simulated moving bed chromatography system (e.g., simulated moving bed chromatography ("SMB"), improved simulated moving bed chromatography, sequential simulated moving bed chromatography and/or related systems) at a first concentration and exit the simulated moving bed chromatography (e.g., with undesired components removed) at a second concentration that is from about 0.1 to about 0.90 times the entering concentration (e.g., such as between about 0.25 to about 0.8, from about 0.3 to about 0.7, or from about 0.40 to about 0.65). Alternatively stated, at least one of the components exits the SMB system at 0.1 to about 0.9 times the concentration of the concentration that it enters the SMB system, for example, if the initial concentration of at least one component in the liquids is 100 g/mL, the final concentration can be from about 10 to about 90 g/L.

In some embodiments, the composition or product, e.g., a purified syrup, has a conductivity at 25 degrees Celsius of less than about 10 microsiemens/cm, e.g., less than 8, 6, 4, or less than 1 microsiemens/cm. In some embodiments, the composition has a conductivity of between about 0.055 and 10, e.g., between about 0.8 and 5 or between about 1 and 3 microsiemens/cm.

In an embodiment, the composition or product has low turbidity, for example measured to be less than about 100 Nephelometric Turbidity Units (NTU) (e.g., less than about 50 NTU, less than about 25 NTU, less than about 10 NTU or less than about 5 NTU). In an embodiment, a composition or product was made by the removal of un-dissolved solids from a preparation. The un-dissolved solids (e.g., residues) can be removed via filtration (e.g., Rotary Vacuum Drum Filtration) and centrifugation (e.g., continuous centrifugation). Some of the dissolved impurities, may be precipitated out by treating the solution with solvents such as methanol, ethanol, isopropanol, acetone, ethyl ether and tetrahydrofuran, and then the precipitates can be removed via filtration or centrifugation. In addition a composition described herein can be formed by removal of enzymes from a preparation. For example, a preparation containing xylose (e.g., containing xylose or a combination of xylose and glucose) can have, for example, up to about 10 wt. % enzymes (e.g., up to about 9 wt. %, up to about 8 wt. %, up to about 5 wt. %, up to about 2 wt. %, up to about 1 wt. %, between about 0.1 and 5 wt. %, between about 1 wt. % and 5 wt. %, between about 2 wt. % and 5 wt. %, between about 0.1 wt. % and 1 wt. %, between about 0.01 wt. % and 1 wt. %, between about 0.001 wt. % and 0.1 wt. %). Enzymes (e.g., parts of enzymes, proteins), can be precipitated by denaturing (e.g., adding an acid, a base, by heating and/or adding solvents). Treatment with carbon dioxide and calcium hydroxide (e.g., over liming) can also be effective in precipitating compounds such as lignin derived products/impurities and enzymes and proteins. In some instances these compounds can be desirable (unwanted) or desirable.

In certain embodiments, the composition or product has a relative sweetness of between about 10 percent and 70 percent of that of sucrose, e.g., between about 10 and about 60 percent, between about 15 and 50 percent or between about 20 and 40 percent of the sweetness of sucrose.

In an embodiment, the composition or product has a viscosity at 20 degrees Celcius of from about 50 to about 100,000 cP. Viscosity is the ratio of shear stress to shear rate, expressed as dynes-second/cm², or poise. A centipoise (cP) is one one-hundredth of a poise.

A composition or product may have a viscosity greater than water (about 1.0 cP at 20° C.), e.g., about 100, 200, 300, 400, 500, 1000, 1500, 2000, 2500, 3000, 3500, 4000, 4500, 5000, 6000, 7000, 8000, 9000 cP or more, e.g., 10,000, 25,000, 50,000, 75,000, 100,000 cP or more, e.g., 200,000 cP. Viscosity may be measured with, e.g., a rheometer or viscometer, though additional methods of measuring viscosity are known in the art.

In particular embodiments, a composition or product described herein comprises a purified saccharide syrups at a concentration of 60 percent by weight saccharides and at a temperature of 20 degrees C. are between about 1,000 and 100,000 cP, e.g., between 2,000 and 75,000 cP or between about 5,000 and 60,000 cP.

Viscosity modifiers may be added to a composition or product described herein. Exemplary viscosity modifiers include, for example, collagen, gellan gum, carbohydrate gel-forming polymers, carob bean gum, locust bean gum, carrageenan, alginates (e.g., alginic acid, sodium alginate, potassium alginate, ammonium alginate, and calcium alginate), agar, guar gum, xanthan gum, carboxymethyl cellulose, clear starch, pectin, gelatin, arrowroot, cornstarch, katakuri starch, potato starch, sago, tapioca, furcellaran, and sodium pyrophosphate. A viscosity modifier may be present in the composition in an amount of from about 0.01% to 10% by weight based on the total volume of the composition (e.g., 0.01, 0.1, 0.5, 1, 2, 3, 4, 5, 6, 7, 8, 9, or 10%), though the viscosity modifier may be present in lower or higher concentrations. In an embodiment, the composition or product is a syrup.

In an embodiment, the composition or product has a glycemic index less than 50, 40, 30, 15 or less, such as less than 10.

In certain embodiments, a composition or product described herein includes a purified saccharide syrup at a concentration of 60 percent by weight, have a viscosity at 20 degrees C. of from about 5,000 to about 75,000 cP, a sweetness of from about 10 to 40 percent of that of sucrose and a glycemic index of from about 10 to about 40.

In an embodiment, the composition or product is formulated as a beverage. By "beverage" is meant a composition that is not in solid or gas form, such as a liquid or semi-liquid that is designed to enter into the mouth of a subject and be orally consumed or ingested. A beverage may be in a ready-to-drink liquid form (e.g., may be consumed without modification) or in a liquid, solid, or concentrated form, which can be transformed into a ready-to-drink liquid form with an addition of another liquid (e.g., water).

In an embodiment, the composition or product includes an additional component selected from one of an electrolyte, sweetener, flavor, vitamin, mineral, amino acid, or preservative.

In some embodiments, the composition or product (e.g., a syrup or beverage) includes a flavor or colorant. In some embodiments, the composition or product (e.g., a syrup or beverage) includes a fragrance. Exemplary flavors, fragrances and colorants include natural and/or synthetic materials. In an embodiment, the flavor, fragrance or colorant is a food grade flavor, fragrance or colorant. These materials can be one or more of a compound, a composition or mixtures of these (e.g., a formulated or natural composition of several compounds). Optionally, the flavors, fragrances, antioxidants and colorants can be derived biologically, for example, from a fermentation process (e.g., fermentation of saccharified materials as described herein). Alternatively, or additionally these flavors, fragrances and colorants can be harvested from a whole organism (e.g., plant, fungus, animal, bacteria or yeast) or a part of an organism. The organism can be collected and or extracted to provide color, flavors, fragrances and/or antioxidant by any means including utilizing the methods, systems and equipment described herein, hot water extraction, supercritical fluid extraction, chemical extraction (e.g., solvent or reactive extraction including acids and bases), mechanical extraction (e.g., pressing, comminuting, filtering), utilizing an enzyme, utilizing a bacteria such as to break down a starting material, and combinations of these methods. The compounds can be derived by a chemical reaction, for example, the combination of a sugar (e.g., as produced as described herein) with an amino acid (Maillard reaction). The flavor, fragrance, antioxidant and/or colorant can be an intermediate and or product produced by the methods, equipment or systems described herein, for example and ester and a lignin derived product.

Some examples of flavor, fragrances or colorants include polyphenols. Polyphenols are pigments responsible for the red, purple and blue colorants of many fruits, vegetables, cereal grains, and flowers. Polyphenols also can have antioxidant properties and often have a bitter taste. The antioxidant properties make these important preservatives. On class of polyphenols are the flavonoids, such as Anthocyanidines, flavanonols, flavan-3-ols, s, flavanones and flavanonols. Other phenolic compounds that can be used include phenolic acids and their esters, such as chlorogenic acid and polymeric tannins.

Among the colorants inorganic compounds, minerals or organic compounds can be used, for example titanium dioxide, zinc oxide, aluminum oxide, cadmium yellow (E.g., CdS), cadmium orange (e.g., CdS with some Se), alizarin crimson (e.g., synthetic or non-synthetic rose madder), ultramarine (e.g., synthetic ultramarine, natural ultramarine, synthetic ultramarine violet), cobalt blue, cobalt yellow, cobalt green, viridian (e.g., hydrated chromium(III)oxide), chalcophylite, conichalcite, cornubite, cornwallite and liroconite. Black pigments such as carbon black and self-dispersed blacks may be used.

Additional examples of flavors, fragrances and colorants are described in WO2014/138553, which is incorporated herein by reference in its entirety.

In an embodiment, the composition or product can include an additional sweetener. Exemplary sweeteners include high fructose corn syrup, mannose, maltose, glucose polymers, sucrose (e.g., cane sugar or beet sugar), glucose, dextrose, lactose, galactose, fructose, polysaccharides (e.g., malodextrins), rice syrup, honey, and natural fruit juices (e.g., orange juice, papaya juice, pineapple juice, apple juice, grape juice, apricot juice, pear juice, tomato juice, agave nectar, or cranberry juice). Additionally, non- or low-caloric sweeteners can be. Examples of such non-caloric or low-caloric sweeteners include, but are not limited to, saccharin, cyclamates, acetosulfam, sorbitol, sucralose, xylitol, erythritol, Stevia extract, L-aspartyl-L-phenyl-alanine ester (e.g., aspartame), L-aspartyl-D-alanine alkyl amides, L-aspartyl-L-1-hydroxymethylalkaneamide, and L-aspartyl-1-hydroxyethylalkaneamide. In an embodiment, a sweetener described herein may be present in a composition or product at a concentration range of about 2% to about 20% by weight based on the total volume of the composition (e.g., 2, 3, 4, 5, 6, 7, 8, 9, 10, 11, 12, 13, 14, 15, 16, 17, 18, 19, or 20%). In an embodiment, a compound, e.g., a beverage described herein is substantially free of a non-caloric or low-calorie sweetener described herein.

In an embodiment a composition or product described herein can include an additional sugar such as glucose. In some embodiments, the composition or product further comprises glucose. In embodiments, the concentration of glucose is at least about 50 g/L (e.g., at least about 100 g/L, at least about 150 g/L, at least about 200 g/L, at least about 250 g/L, at least about 300 g/L, at least about 350 g/L, at least about 400 g/L, at least about 450 g/L). In an embodiment, a composition described herein has a concentration of glucose of from about 50 g/L to about 500 g/L, such as from about 100 g/L to about 400 g/L, from about 150 g/L to about 350 g/L or from about 175 g/L to about 275 g/L. In embodiments, wherein the composition or product includes glucose, the ratio of xylose to glucose in the composition can be, for example, from about 10:1 to about 1:10, e.g., from about 8:1 to about 1:8 from about 5:1 to about 1:5, from about 3:1 to about 1:3, from about 2:1 to about 1:2, or about 1:1. In some embodiments, the ratio of xylose/glucose is between about 30/50 and about 1000/50, e.g., between about 35/50 and about 250/50, between about 40/50 and about 100/50 or between about 45/50 and about 95/50. In preferred embodiments, the ratio of xylose/glucose is between about 40/50 to about 95/50, e.g., between about 45/50 and about 90/50. Even small amounts of xylose can have a positive impact on health.

In an embodiment, a composition or product such as a beverage, includes an electrolyte. Exemplary electrolytes include potassium salts, chloride salts, bromide salts, sodium salts, magnesium salts, calcium salts, citrate salts, acetate salts, phosphate salts, salicylates, bicarbonate salts, lactate salts, sulphate salts, tartrate salts, benzoate salts, selenite salts, molybdate salts, iodide salts, oxides, and combinations thereof. An electrolyte may be present in a composition at a concentration range of about 0.01% to about 10% by weight based on the total volume of the composition (e.g., 0.01, 0.02, 0.03, 0.04, 0.05, 0.1, 0.5, 1, 2, 3, 4, 5, 6, 7, 8, 9, or 10).

In an embodiment, a composition or product described herein includes a vitamin or mineral. Exemplary vitamins and minerals that may be included in the compositions described herein include, e.g., choline bitartate, niacinamide, thiamin, folic acid, d-calcium pantothenate, biotin, vitamin A, vitamin C, vitamin $B_1$ hydrochloride, vitamin $B_2$, vitamin $B_3$, vitamin $B_6$ hydrochloride, vitamin $B_{12}$, vitamin D, vitamin E acetate, vitamin K, and salts of calcium, potassium, magnesium, zinc, iodine, iron, and copper. When included in a composition of the invention, the composition contains at least 5, 10, 15, 20, 25, 30, 35, 40, 45, or 50% of the U.S. recommended daily intake (RDI) for such vitamins and minerals.

In an embodiment, a composition or product described herein includes a preservative. Exemplary preservatives include, for example, sorbate, benzoate, and polyphosphate preservatives (e.g., sorbic acid, benzoic acid, calcium sorbate, sodium sorbate, potassium sorbate, calcium benzoate, sodium benzoate, potassium benzoate, and mixtures thereof). When included in a composition, the preservative can be at levels from about 0.0005% to about 0.5% (e.g., 0.0005, 0.001, 0.005, 0.01, 0.05, 0.1, or 0.5%) by weight based on the total volume of the composition.

In an embodiment, a composition or product described herein includes an antioxidant. Exemplary antioxidants include vitamin C and vitamin E; beta-carotene, lutein, or other carotenoids; cyanidin, delphinidin, malvidin, or other anthocyanidins; apigenin, luteolin, or other flavones; hesperitin, naringenin, or other flavonones; isorhamnetin, quercetin, kaempferol or other flavonols; and epigallocatechin-3-gallate, epicatechin, thearubigins, or other flavan-3-ols.

In an embodiment, a composition or product described herein includes an amino acid (e.g., leucine, isoleucine, lysine, methionine, phenylalanine, threonine, tryptophan, and valine), a stimulant (e.g., caffeine), an mulsifying agent, carbon dioxide (e.g., to carbonate a liquid composition), a stabilizer, a humectant, an anticaking agents, or an extract such as an herbal extract.

In certain embodiments of any compositions or products described herein, the composition or product is a beverage or gel that is made by reconstituting a dry powder with an aqueous fluid (e.g., water).

In some instances, any composition or product described herein can include fibers, such as cellulosic and lignocellulosic fibers, such as any of those described herein.

In other embodiments of any compositions or products described herein, the composition or product is a packaged beverage. In some embodiments, the packaged beverage is provided in a unit that contains between 10-1000 mL (e.g., between 10-500 mL) of the beverage.

The compositions or products described herein may be bottled or packaged in, for example, glass bottles, plastic bottles and containers (e.g., polyethylene terephthalate or foil-lined ethylene vinyl alcohol), metal cans (e.g., coated aluminum or steel), lined cardboard containers, pouches, packs, wrappers, or any other packaging known to one of skill in the art. For example, a ready-to-drink beverage can be bottled or packaged in a unit that contains between 10-1000 mL of the beverage. For example, the packaging can contain 10, 20, 50, 100, 200, 300, 400, 500, 600, 700, 800, 900, or 1000 mL of the beverage. Alternatively, the packaging can contain 200, 250, 330, 350, 355, 375, 440, or 500 mL of the beverage. A ready-to-drink beverage can also be bottled or packaged in a unit that contains between 1-32 fluid ounces of beverage (e.g., the unit may contain 1, 2, 5, 6.75, 8, 8.3, 8.4, 8.45, 9.6, 10, 12, 15, 15.5, 16, 18.6, 20, 23, 24, or 32 fluid ounces). Where a shelf-stable composition or solution is desired, the packaging is appropriately sterilized before being filled by the pasteurized, ultra-pasteurized, or sterilized composition or solution. Where required for mutual stability of two or more components (for example if a component is unstable at low pH), the packaging may feature multiple containers that can be mixed shortly before ingestion or that can be consumed serially.

Methods of Making

A composition or product described herein can be made using a process described herein. For example, a composition described herein can be made by converting or processing a biomass into a composition comprising xylose. In some embodiments, the composition comprises xylose and glucose. Exemplary methods include those described in WO2014/138553, which is incorporated by reference herein.

Methods for converting a biomass to products, such as sugar products, are known in the art, for example, as described in US Patent Application 2014/0011258, the contents of which are incorporated by reference in its entirety. Briefly, a biomass is optimally pretreated, e.g., to reduce the recalcitrance, and saccharified by a saccharification process that involves incubating the treated biomass with biomass-degrading, or cellulolytic, enzymes to produce sugars (e.g., glucose and/or xylose). The sugar products can then be further processed to produce a final product, e.g., by fermentation or distillation.

Using the processes described herein, the biomass material can be converted in a cost efficient manner to a composition described herein.

Biomass

The biomass may include, but is not limited to starchy materials, sugar cane, agricultural waste, paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, plankton manure, sewage, offal, agricultural or industrial waste, arracacha, buckwheat, banana, barley, cassava, kudzu, oca, sago, sorghum, potato, sweet potato, taro, yams, beans, favas, lentils, peas, or mixtures of any of these. In a preferred embodiment, the biomass comprises agriculture waste, such as corn cobs, e.g., corn stover. In another embodiment, the biomass comprises grasses.

In one embodiment, the biomass is treated prior to contact with the compositions described herein. For example, the biomass is treated to reduce the recalcitrance of the biomass, to reduce its bulk density, and/or increase its surface area. Suitable biomass treatment process may include, but are not limited to: bombardment with electrons, sonication, oxidation, pyrolysis, steam explosion, chemical treatment, mechanical treatment, and freeze grinding. Preferably, the treatment method is bombardment with electrons.

In some embodiments, electron bombardment is performed until the biomass receives a total dose of at least 0.5 Mrad, e.g. at least 5, 10, 20, 30, or at least 40 Mrad. In some embodiments, the treatment is performed until the biomass receives a dose a of from about 0.5 Mrad to about 150 Mrad, about 1 Mrad to about 100 Mrad, about 5 Mrad to about 75 Mrad, about 2 Mrad to about 75 Mrad, about 10 Mrad to about 50 Mrad, e.g., about 5 Mrad to about 50 Mrad, about 20 Mrad to about 40 Mrad, about 10 Mrad to about 35 Mrad, or from about 20 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 9 Mrad/pass can in some cases cause thermal degradation of the feedstock material.

The biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution. The enzymes can be made/induced according to the methods described herein.

Specifically, the enzymes can be supplied by organisms that are capable of breaking down biomass (such as the cellulose and/or the lignin portions of the biomass), or that contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Saccharification

The reduced-recalcitrance biomass is treated with the biomass-degrading enzymes discussed above, generally by combining the reduced-recalcitrance biomass and the biomass-degrading enzymes in a fluid medium, e.g., an aqueous solution. In some cases, the feedstock is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

Provided herein are mixtures of enzymes that are capable of degrading the biomass, e.g., an enzyme mixture of biomass-degrading enzymes, for use in the saccharification process described herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

In a preferred embodiment, the saccharification reaction occurs at a pH optimal for the enzymatic reactions to occur, e.g., at the pH optimal for the activity of the biomass-degrading enzymes. Preferably, the pH of the saccharification reaction is at pH 4-4.5. In a preferred embodiment, the saccharification reaction occurs at a temperature optimal for the enzymatic reactions to occur, e.g., at the temperature optimal for the activity of the biomass-degrading enzymes. Preferably, the temperature of the saccharification reaction is at 42° C.-52° C.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

In the processes described herein, for example after saccharification, xylose (e.g., glucose and xylose) can be isolated. For example, xylose can be isolated by precipitation, crystallization, chromatography (e.g., simulated moving bed chromatography, high pressure chromatography), centrifugation, extraction, any other isolation method known in the art, and combinations thereof. In an embodiment, the isolate product includes xylose or a mixture of glucose. Once isolated, the xylose containing composition, or xylose and glucose containing composition can be formulated into a product described herein such as a beverage or a syrup.

Other examples of suitable biomass-degrading enzymes for use in the enzyme mixture of the present invention include the enzymes from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435,307), *Coprinus cinereus, Fusarium oxysporum, Myceliophthora thermophila, Menpilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum*, and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Biomass-degrading enzymes may also be obtained from *Chrysosporium*, preferably a strain of *Chrysosporium lucknowense*. Additional strains that can be used include, but are not limited to, *Trichoderma* (particularly *T. viride, T. reesei*, and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

In embodiments, the microorganism is induced to produce the biomass-degrading enzymes described herein under conditions suitable for increasing production of biomass-degrading enzymes compared to an uninduced microorganism. For example, an induction biomass sample comprising biomass as described herein is incubated with the microorganism to increase production of the biomass-degrading enzymes. Further description of the induction process can be found in US 2014/0011258, the contents of which are hereby incorporated by reference in its entirety.

The biomass-degrading enzymes produced and/or secreted by the aforementioned microorganisms can be isolated and added to the enzyme mixture of the present invention. Alternatively, in one embodiment, the aforementioned microorganisms or host cells expressing the biomass-degrading enzymes described herein and above are not lysed before addition to the saccharification reaction.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

EQUIVALENTS

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

What is claimed is:

1. A composition comprising an enzymatically saccharified cellulosic or lignocellulosic biomass extract, said biomass having a source xylose and glucose ratio based on both free sugar and polysaccharides of the biomass,
    wherein the composition comprises molecular glucose, molecular xylose and one or more saccharides selected from the group consisting of galactose, sucrose, arabinose, mannose, and fructose,
    wherein the glucose, xylose and one or more saccharides are co-produced from the source biomass,
    wherein the xylose/glucose ratio of the composition is the same ratio as the source xylose/glucose ratio of the cellulosic or lignocellulosic biomass,
    wherein less than 5 percent by weight of the composition comprises the one or more saccharides, and
    wherein the composition further comprises a preservative, an emulsifying agent, a stabilizer, a humectant, or an anticaking agent.

2. The composition of claim 1, wherein the composition is a food grade product.

3. The composition of claim 1, wherein the composition is a cosmetic grade product.

4. The composition of claim 1, wherein the composition is a medical grade product.

5. The composition of claim 1, wherein the ratio of xylose/glucose is between about 35/50 and about 250/50.

6. The composition of claim 1, wherein the ratio of xylose/glucose is between about 40/50 and about 100/50.

7. The composition of claim 1, wherein the ratio of xylose/glucose is between about 45/50 and about 95/50.

8. The composition of claim 1, wherein the glycemic index of the composition is less than 30.

9. The composition of claim 1, wherein the glycemic index of the composition is less than 50.

10. The composition of claim 1, wherein the glycemic index of the composition is less than 15.

11. The composition of claim 1, wherein less than 1 percent by weight of the composition comprises the one or more saccharides.

12. The composition of claim 1, wherein less than 5 percent of the calorie content of the composition is from the one or more saccharides.

13. The composition of claim 1, wherein less than 1 percent of the calorie content of the composition is from the one or more saccharides.

14. The composition of claim 1, further comprising a colorant.

15. The composition of claim 1, further comprising an electrolyte.

16. The composition of claim 1, further comprising a vitamin.

17. The composition of claim 1, wherein the composition is in a form selected from capsule, pill, or tablet.

18. The composition of claim 1, wherein the composition is a solution.

19. The composition of claim 10, wherein the solution has a viscosity in the range of 50-100,000 cP.

20. The composition of claim 10, wherein the composition is a syrup.

21. The composition of claim 1, wherein the composition is a solid.

22. The composition of claim 1, wherein the composition has a color less than about 100 as measured by the platinum-Cobalt method.

23. A composition comprising an enzymatically saccharified cellulosic or lignocellulosic biomass extract, said biomass having a source xylose and glucose ratio based on both free sugar and polysaccharides of the biomass,
    wherein the composition comprises molecular glucose, molecular xylose, wherein the composition xylose/glucose ratio is the same ratio as the source xylose/glucose ratio of the cellulosic or lignocellulosic biomass; and
    one or more of a saccharide selected from the group consisting of galactose, sucrose, arabinose, mannose, and fructose,
    wherein less than 5 percent by weight of the composition comprises the one or more saccharides, and
    wherein the composition further comprises a preservative, an emulsifying agent, a stabilizer, a humectant, or an anticaking agent.

24. The composition of claim 23, wherein the ratio of xylose/glucose is between about 35/50 and about 250/50, between about 40/50 and about 100/50, or between about 45/50 and about 95/50.

25. The composition of claim 23, wherein the glycemic index of the composition is less than 50.

26. The composition of claim 23, wherein less than 1 percent by weight of the composition comprises the one or more saccharides.

27. The composition of claim 23, wherein less than 5 percent of the calorie content of the composition is from the one or more saccharides.

28. The composition of claim 1, wherein the composition is a product selected from the group consisting of a cosmetic product, oral care product, therapeutic product, nutraceutical product, diagnostic, beverage, animal food product, and human food product.

29. A composition comprising an enzymatically saccharified cellulosic or lignocellulosic biomass extract, said biomass having a source xylose and glucose ratio based on both free sugar and polysaccharides of the biomass,
   wherein the composition comprises molecular glucose, molecular xylose and one or more saccharides selected from the group consisting of galactose, sucrose, arabinose, mannose, and fructose,
   wherein the glucose, xylose and one or more saccharides are co-produced from the source biomass,
   wherein the xylose/glucose ratio of the composition is the same ratio as the source xylose/glucose ratio of the cellulosic or lignocellulosic biomass,
   wherein the glycemic index of the composition is less than 50, and
   wherein the composition further comprises a preservative, an emulsifying agent, a stabilizer, a humectant, or an anticaking agent.

30. The composition of claim 29, wherein the ratio of xylose/glucose is between about 35/50 and about 250/50, between about 40/50 and about 100/50, or between about 45/50 and about 95/50.

31. The composition of claim 29, wherein the glycemic index of the composition is less than 30.

32. The composition of claim 29, wherein less than 1 percent by weight of the composition comprises the one or more saccharides.

33. The composition of claim 29, wherein less than 5 percent of the calorie content of the composition is from the one or more saccharides.

* * * * *